(12) United States Patent
Englebienne et al.

(10) Patent No.: US 7,618,560 B2
(45) Date of Patent: Nov. 17, 2009

(54) STABLE METAL/CONDUCTIVE POLYMER COMPOSITE COLLOIDS AND METHODS FOR MAKING AND USING THE SAME

(75) Inventors: Patrick Englebienne, Zingem (BE); Anne Van Hoonacker, Zingem (BE)

(73) Assignee: Pharma Diagnostics N.V., Zingem (BE)

( * ) Notice: Subject to any disclaimer, the term of this patent is extended or adjusted under 35 U.S.C. 154(b) by 544 days.

(21) Appl. No.: 11/264,353

(22) Filed: Oct. 20, 2005

(65) Prior Publication Data

US 2007/0172834 A1 Jul. 26, 2007

Related U.S. Application Data

(60) Provisional application No. 60/621,258, filed on Oct. 21, 2004.

(51) Int. Cl.
 H01B 1/02 (2006.01)
 H01B 1/12 (2006.01)
(52) U.S. Cl. .............. 252/514; 252/500; 252/520.3; 252/512
(58) Field of Classification Search ............ 252/514, 252/500, 520.3, 512
 See application file for complete search history.

(56) References Cited

U.S. PATENT DOCUMENTS

| | | | |
|---|---|---|---|
| 5,011,956 A | | 4/1991 | Ford et al. |
| 6,165,386 A | * | 12/2000 | Endo et al. ............ 252/500 |
| 6,369,206 B1 | | 4/2002 | Leone et al. |
| 6,645,721 B2 | | 11/2003 | Mirkin et al. |
| 6,656,388 B1 | * | 12/2003 | Yang et al. ............ 252/500 |
| 6,808,936 B1 | * | 10/2004 | Englebienne et al. ...... 436/506 |
| 6,989,239 B2 | * | 1/2006 | Fremont et al. ........... 435/7.24 |
| 7,056,675 B2 | * | 6/2006 | Samuelson et al. ........... 435/6 |
| 2003/0211488 A1 | | 11/2003 | Mirkin et al. |
| 2004/0038255 A1 | | 2/2004 | Mirkin et al. |
| 2004/0222413 A1 | * | 11/2004 | Hsu et al. ............... 257/40 |

FOREIGN PATENT DOCUMENTS

EP 0 623 822 11/1994
WO WO 02/087749 A1 * 11/2002

OTHER PUBLICATIONS

Derwent Acc. No. 1994-218293, Nov. 1999.*
Englebienne "Synthetic Materials Capable of Reporting Biomolecular Recognition Events by Chromic Transition," J. Mater. Chem (1999) 9:1043-1054.
Englebienne et al. "Water-Soluble Conductive Polytmer Homogeneous Immunoassay (SOPHIA): A Novel Immunoassay Capable of Automation," Journal of Immunological Methods (1996) 191:159-170.
Englebienne "Use of Colloidal Gold Surface Plasmon Resonance Peak Shift to Infer Affinity Constants from the Interactions Between Protein Antigens and Antibodies Specific for Single or Multiple Epitopes," Analyst (1998) 123:1599-1603.
Englebienne et al. "High-Throughput Screening Using the Surface Plasmon Resonance Effect of Colloidal Gold Nanoparticles," The Royal Society of Chemistry (2001) 126:1645-1651.
Englebienne et al. "Surface Plasmon Resonance: Principles, Methods and Applications in Biomedical Sciences," Spectroscopy (2003) 17:255-273.
Englebienne et al. "Advances in High-Throughput Screening: Biomolecular Interaction Monitoring in Real-Time with Colloidal Metal Nanoparticles," Combinatorial Chemistry & High Throughput Screening (2003) 6:777-787.
Kerman et al. "Electrochemical Coding of Single-Nucleotide Polymorphisms by Monobase-Modified Gold Nanoparticles," Anal. Chem. (2004) 76:1877-1884.
Khlebtsov et al. "A Multilayer Model for Gold Nanoparticle Bioconjugates: Application to Study of Gelatin and Human IgC Adsorption Using Extinction and Light Scattering Spectra and the Dynamic Light Scattering Method," Colloid Journal (2003) 65(5):622-635.
Walton et al. "Particles for Multiplexed Analysis in Solution: Detection and Identification of Striped Metallic Particles Using Optical Microscopy," Anal. Chem. (2002) 74:2240-2247.

* cited by examiner

*Primary Examiner*—Douglas Mc Ginty
(74) *Attorney, Agent, or Firm*—Bret E. Field; Bozicevic, Field & Francis LLP

(57) ABSTRACT

Stable metal/conductive polymer composite colloids and methods for making the same are provided. The subject colloids find use in a variety of different applications, including analyte detection applications. Also provided are kits that include the subject colloids.

31 Claims, 12 Drawing Sheets

US 7,618,560 B2

STABLE METAL/CONDUCTIVE POLYMER COMPOSITE COLLOIDS AND METHODS FOR MAKING AND USING THE SAME

CROSS-REFERENCE TO RELATED APPLICATIONS

This application claims priority under 35 U.S.C. § 119(e) to U.S. Provisional Application Ser. No. 60/621,258 filed on Oct. 21, 2004; the disclosure of which is herein incorporated by reference.

INTRODUCTION

Background of the Invention

Nanoparticles of noble metals such as gold or silver can be prepared in various geometrical forms such as spheres, rods or pyramids. These small objects contain the metallic element in chemically reduced form and depending on the way they are prepared, they can be either stored as reduced powdered solids, or held in stable suspension in solvents such as water or various organic solvents (i.e., as a colloid). Because of the nanometer size of the particles, the naked eye cannot distinguish such suspensions from true solutions, although the microscope can, and such suspensions are therefore termed colloidal solutions. The particles are therefore easily cast on various supports to form well-defined circuits.

The study of these metal nanoparticles has been an extremely active area in recent years because of their unique electronic, optical and catalytic properties. Since light is associated with an electromagnetic field, the opto-electronic properties of the nanoparticles are particularly interesting. Indeed, because they are metallic and capable of conducting electricity, the noble metal nanoparticles are surrounded at their surface by a dense cloud of conducting electrons. When these electrons are excited by light, the electromagnetic radiation combines with these electrons to form collective oscillations that radiate away from the particle surface. As a result, the particles exhibit specific light absorption, reflection, emission and scattering properties that can be successfully applied in various fields such as analyte detection, electron transport or information storage. Most of the particles studied so far are homogeneously made of the same metal. However, it has been shown recently that it was possible to construct nano-objects made of different metals alternating in the structure. This new advance opens the way to their use as nano bar-codes in numerous applications.

Because of the field acknowledge potential of nanoparticles in a variety of diverse applications, there is continued interest in the development of new types of nanoparticles and applications therefore.

SUMMARY OF THE INVENTION

Stable metal/conductive polymer composite colloids and methods for making the same are provided. The subject colloids find use in a variety of different applications, including analyte detection applications. Also provided are kits that include the subject colloids.

DEFINITIONS

Figure 1:
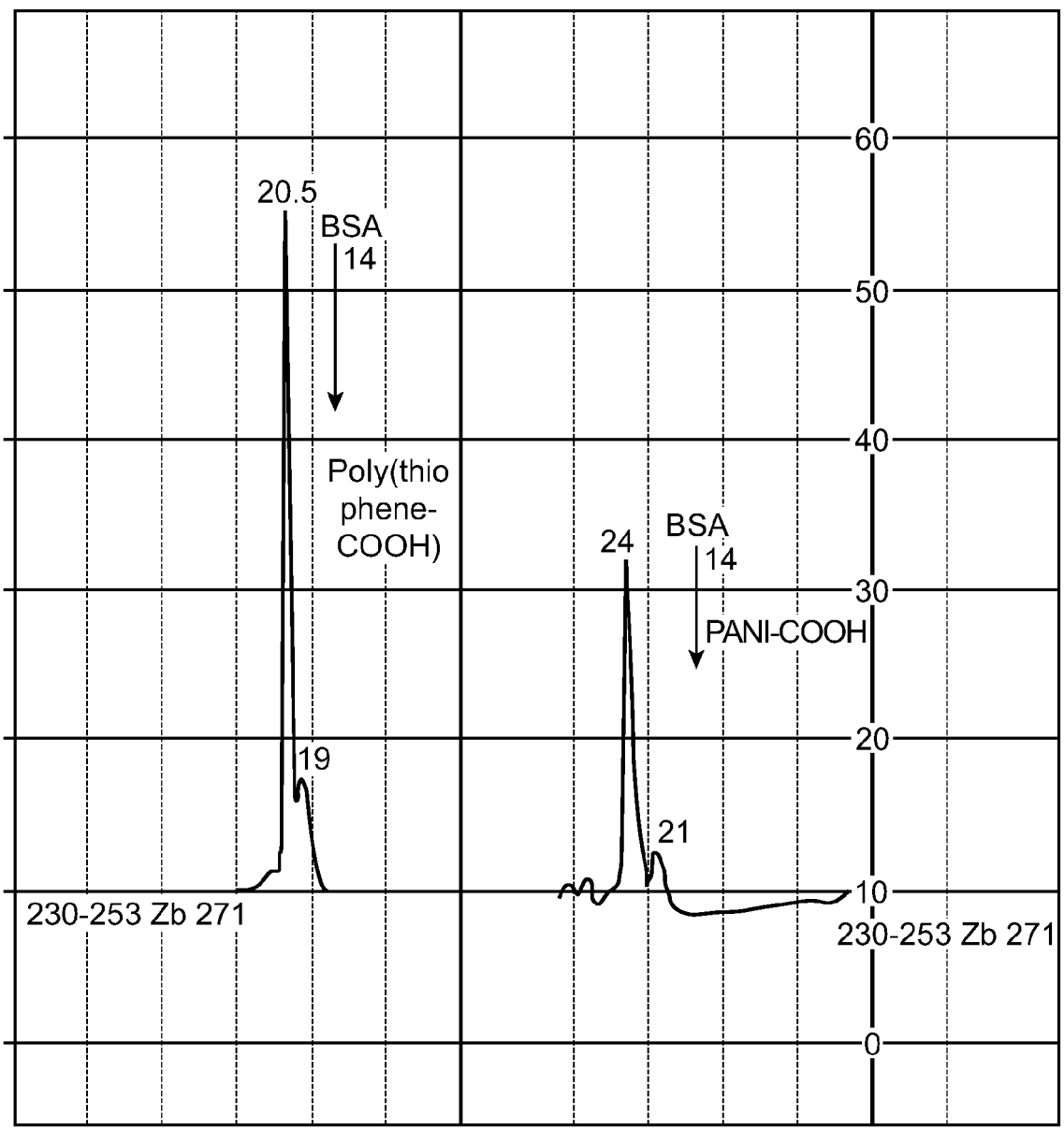
FIG. 1. GP-HPLC profile of poly(thiophene-3-carboxylic acid) [left] and of PANI-COOH [right] solutions. The elution time of bovine serum albumin (BSA) is indicated (arrow) for reference.

Unless defined otherwise, all technical and scientific terms used herein have the same meaning as commonly understood by one of ordinary skill in the art to which this invention belongs. Still, certain elements are defined below for the sake of clarity and ease of reference.

The term "colloid" refers to a fluid composition of microscopic particles suspended in a liquid medium. In representative colloids, the particles therein are between one nanometer and one micrometer in size.

The term metal colloid refers to a colloid in which the suspended microscopic particles are metal particles.

The term "noble metal" refers to Group VIII metals of the Periodic Table including, but not limited to: platinum, iridium, palladium and the like, as well as gold, silver etc.

The term "conductive polymer" means an electrically conductive polymeric material. In representative embodiments, conductive polymers are organic polymers, such as p-conjugated organic polymers. For example, employed may be polypyrroles such as polypyrrole, poly(N-substituted pyrrole), poly(3-substituted pyrrole), and poly(3,4-disubstituted pyrrole); polythiophenes such as polythiophene, poly(3-substituted thiophene), poly(3,4-disubstituted thiophene), and polybenzothiophene; polyisothianaphthenes such as polyisothianaphthene; polythienylenevinylenes such as polythienylenevinylene; poly(p-phenylenevinylenes) such as poly(p-phenylenevinylene); polyanilines such as polyaniline, poly(N-substituted aniline), poly(3-substituted aniline), and poly (2,3-substituted aniline); polyacetylenes such as polyacetylene; polydiacetylenes such as polydiacetylene; polyazulenes such as polyazulene; polypyrenes such as polypyrene; polycarbazoles such as polycarbazole and poly(N-substituted carbazole), polyselenophenes such as polyselenophene; polyfurans such as polyfuran and polybenzofuran; poly(p-phenylens) such as poly(p-phenylene); polyindoles such as polyindole; polypyridazines such as polypyridazine; polyacenes such as naphthacene, pentacene, hexacene, heptacene, dibenzopentacene, tertabenzopentacene, pyrene, dibenzopyrene, chrysene, perylene, coronene, Terylene, ovalene, quoterylene, and circumanthracene; derivatives (such as triphenodioxazine, triphenodithiazine, hexacene-6, 15-quinone) which are prepared by substituting some of carbon atoms of polyacens with atoms such as N, S, and O, or a functional group such as a carbonyl group; polymers such as polyvinylcarbazoles, polyphenylenesulfide, and polyvinylenesulfide. Of particular interest in representative embodiments are polypyrrole, polythiophene, polyaniline or their derivatives.

As is known in the art, the conducting polymer may be doped by incorporating into the polymer materials having a functional group such as a dimethylamino group, a cyano group, a carboxyl group and a nitro group, materials such as benzoquinone derivatives, and tetracyanoethylene as well as tetracyanoquinodimethane, and derivatives thereof, which work as an acceptor which accepts electrons, or, for example, materials having a functional group such as an amino group, a triphenyl group, an alkyl group, a hydroxyl group, an alkoxy group, and a phenyl group; substituted amines such as phenylenediamine; anthracene, benzoanthracene, substituted benzoanthracenes, pyrene, substituted pyrene, carbazole and derivatives thereof, and tetrathiafulvalene and derivatives thereof, which work as a donor which is an electron donor. The doping, as described herein, means that electron accepting molecules (acceptors) or electron donating molecules (donors) are incorporated in said thin film employing doping. Employed as dopants used in the present invention may be either acceptors or donors The term "metal/conductive polymer composite colloid" refers to a colloid made up of metal particles having a conductive polymer present on a surface thereof.

The term "adsorb" refers to the adhesion in an extremely thin layer of molecules (e.g., water-soluble polymer molecules) to the surfaces of solid bodies, e.g., metal particles, with which they are in contact.

A material is "water-soluble" if it dissolves in water. With respect to the conductive polymers of the present invention, such are considered water-soluble if at least about 0.02 g will dissolve in at least about 100 ml water at standard temperature and pressure (STP) conditions.

As used herein, the term "contacting" means to bring or put together. As such, a first item is contacted with a second item when the two items are brought or put together, e.g., by touching them to each other. The term "combining" refers to contacting two different compositions in a manner such that they become a single composition.

The term "agitation" refers to application of physical movement to a composition, such that the components thereof move relative to each other. As such, the term agitation is employed broadly to refer to mixing, stirring, and the like.

The term "ligand" as used herein refers to any type of molecule that is a member of a specific binding pair. Ligands of interest include, but are not limited to biomolecules, where the term "biomolecule" means any organic or biochemical molecule, group or species of interest, e.g., that can specifically bind to an analyte of interest. Exemplary biomolecules include peptides, proteins, amino acids and nucleic acids, small organic and inorganic molecules, etc.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than about 10 to about 20 residues. The terms "polypeptide" and "protein" may be used interchangeably.

The term "protein" as used herein refers to polypeptides of specific sequence of more than about 50 residue and includes D and L forms, modified forms, etc.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

Also of interest are small organic and inorganic molecules. For example, organic molecules, such small organic compounds having a molecular weight of more than 50 and less than about 2,500 daltons are of interest as ligands in certain embodiments. Small organic compounds may include functional groups necessary for structural interaction with proteins, particularly hydrogen bonding, and typically include at least an amine, carbonyl, hydroxyl or carboxyl group, preferably at least two of the functional chemical groups. Such compounds may include cyclical carbon or heterocyclic structures and/or aromatic or polyaromatic structures substituted with one or more of the above functional groups.

In certain embodiments, a linking group is employed to indirectly bind a ligand to a surface of a composite nanoparticle. Where linking groups are employed, such groups are chosen to provide for covalent attachment of the ligand moiety and the surface through the linking group. Linking groups of interest may vary widely depending on the nature of the target and blocking ligand moieties. A variety of linking groups are known to those of skill in the art and find use in the subject bifunctional molecules. Generally, such linkers will comprise a spacer group terminated at either end with a reactive functionality capable of covalently bonding to the ligand or surface. Spacer groups of interest possibly include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject bifunctional molecules include heterofunctional compounds, such as azidobenzoyl hydrazide, N-[4-(p-azidosalicylamino)butyl]-3'-[2'-pyridyldithio)propionamid), bis-sulfosuccinimidyl suberate, dimethyladipimidate, disuccinimidyltartrate, N-maleimidobutyryloxysuccinimide ester, N-hydroxy sulfosuccinimidyl 4-azidobenzoate, N-succinimidyl[4-azidophenyl]-1,3'-dithiopropionate, N-succinimidyl[4-iodoacetyl]aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The terms "ribonucleic acid" and "RNA" as used herein refer to a polymer composed of ribonucleotides.

By "homogenous" is meant that a composition is of the same or a similar kind or nature throughout, i.e., of uniform structure or composition throughout.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

A "biopolymer" is a polymer of one or more types of repeating units. Biopolymers are typically found in biological systems (although they may be made synthetically) and may include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a "biopolymer" may include DNA (including cDNA), RNA, oligonucleotides, and PNA and other polynucleotides as described in U.S. Pat. No. 5,948,902 and references cited therein (all of which are incorporated herein by reference), regardless of the source.

The phrase "optical property" refers to an optical parameter, i.e., a property whose value determines the characteristic or behavior of something, where representative optical properties include, but are not limited to: light absorption, light emission, light reflection and light scattering.

The terms "reference" and "control" are used interchangeably to refer to a known value or set of known values against which an observed value may be compared. As used herein, known means that the value represents an understood parameter, e.g., light absorption, light emission, etc.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the term "detecting" means to ascertain a signal, either qualitatively or quantitatively.

The term "binding" refers to two objects associating with each other to produce a stable composite structure. In certain embodiments, binding between two complementary nucleic acids may be referred to as specifically hybridizing. The terms "specifically hybridizing," "hybridizing specifically to" and "specific hybridization" and "selectively hybridize to," are used interchangeably and refer to the binding, duplexing, or hybridizing of a nucleic acid molecule preferentially to a particular nucleotide sequence under stringent conditions.

The term "screening" refers to determining the presence of something of interest, e.g., an analyte, an occurrence, etc. As used herein, the term "determining" means to identify, i.e., establishing, ascertaining, evaluating or measuring, a value for a particular parameter of interest, e.g., a hybridization parameter. The determination of the value may be qualitative (e.g., presence or absence) or quantitative, where a quantitative determination may be either relative (i.e., a value whose units are relative to a control (i.e., reference value) or absolute (e.g., where a number of actual molecules is determined).

The term "sample" as used herein refers to a fluid composition, where in certain embodiments the fluid composition is an aqueous composition.

DESCRIPTION OF THE SPECIFIC EMBODIMENTS

Stable metal/conductive polymer composite colloids and methods for making the same are provided. The subject colloids find use in a variety of different applications, including analyte detection applications. Also provided are kits that include the subject colloids.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention provides stable metal/conductive polymer composite colloids and methods for making and using the same. In further describing the subject invention, representative embodiments of the subject colloids are reviewed first in greater detail, followed by a discussion of representative fabrication protocols and methods for using the subject colloids. In addition, a review of representative kits that include the subject colloids is provided.

Metal/Conductive Polymer Composite Colloids

As summarized above, the present invention provides metal/conductive polymer composite colloids. A feature of the subject colloids is that they are stable. As used herein, the term stable refers to the ability of the particles of the colloid to remain in suspension in the carrier medium of the colloid, e.g., the particles do not precipitate out of suspension to any significant extent. With respect to the subject colloids, the colloids are stable when maintained at STP conditions for a period of time that is at least about 1 month long, such as at least about 3 months long, including at least about 6 months long, and are, in representative embodiments, stable for periods of up to one year or longer, such as up to two years or longer, including up to five years or longer.

As the subject colloids are composites of metals and conducting polymers, they include both a metal component and a conducting polymer component. The metal component of the subject colloids is, in representative embodiments, a noble metal. As indicated above, noble metals of interest include, but are not limited to: Group VIII metals of the Periodic Table including, but not limited to: platinum, iridium, palladium and the like, as well as gold, silver etc.

The term "conductive polymer" means an electrically conductive polymeric material. In representative embodiments, conductive polymers are organic polymers, such as p-conjugated organic polymers. For example, employed may be polypyrroles such as polypyrrole, poly(N-substituted pyrrole), poly(3-substituted pyrrole), and poly(3,4-disubstituted pyrrole); polythiophenes such as polythiophene, poly(3-substituted thiophene), poly(3,4-disubstituted thiophene), and polybenzothiophene; polyisothianaphthenes such as polyisothianaphthene; polythienylenevinylenes such as polythienylenevinylene; poly(p-phenylenevinylenes) such as poly(p-phenylenevinylene); polyanilines such as polyaniline, poly(N-substituted aniline), poly(3-substituted aniline), and poly(2,3-substituted aniline); polyacetylenes such as polyacetylene; polydiacetylenes such as polydiacetylene; polyazulenes such as polyazulene; polypyrenes such as polypyrene; polycarbazoles such as polycarbazole and poly(N-substituted carbazole), polyselenophenes such as polyselenophene; polyfurans such as polyfuran and polybenzofuran; poly(p-phenylens) such as poly(p-phenylene); polyindoles such as polyindole; polypyridazines such as polypyridazine; polyacenes such as naphthacene, pentacene, hexacene, heptacene, dibenzopentacene, tertabenzopentacene, pyrene, dibenzopyrene, chrysene, perylene, coronene, Terylene, ovalene, quoterylene, and circumanthracene; derivatives (such as triphenodioxazine, triphenodithiazine, hexacene-6, 15-quinone) which are prepared by substituting some of carbon atoms of polyacens with atoms such as N, S, and O, or a functional group such as a carbonyl group; polymers such as polyvinylcarbazoles, polyphenylenesulfide, and polyvinylenesulfide. Of particular interest in representative embodiments are polypyrrole, polythiophene, polyaniline or their derivatives. In representative embodiments, the polymer is a water-soluble conducting polymer. In certain of these embodiments, the water-soluble conducting polymer is a substituted organic conducting polymer, where the polymer comprises an ionizable group or groups. By ionizable group is meant a moiety that, at an appropriate pH is capable of carrying a net positive or negative charge. Ionizable groups of interest include, but are not limited to: carboxyl groups, amino groups, etc. In certain embodiments, the water-soluble conducting polymer is a substituted polyaniline, such as a polyaniline substituted with ionizable groups, e.g., carboxyl groups, such as poly(aniline-2-carboxylic acid).

In the subject colloids, metal particles are surface coated with a conducting polymer and suspended in a liquid medium, typically an aqueous medium. By "surface coated" is meant that at least a portion of the surface of the particles, if not the entire surface of the particles, is covered with a layer of conducting polymer molecules. In representative embodiments, the layer or coating of conducting polymer is a monolayer, such that a single layer of polymer molecules covers the surface of the particles.

The dimensions of the particles may vary, but in representative embodiments range from about 1 nm to about 1 micrometer, such as from about 1 nm to about 100 nm, including from about 30 nm to about 60 nm. In representative embodiments, the particles have a narrow particle size distribution. By narrow particle size distribution is meant that the standard deviation of the particles does not exceed about 30%, and in certain representative embodiments does not exceed about 20%, e.g., does not exceed about 17%, including does not exceed about 10% of the average diameter.

With respect to the polymer component of the subject composites, the polymer component has an average molecular weight ranging from about 1,500 Da to about 32,000 Da, such as from about 5,000 Da to about 7,000 Da, including from about 23,000 Da to about 27,000 Da. The polymer component is further characterized by having a narrow size dispersity, such that at least about 45 number %, particularly at least about 25 number % of the polymer molecules adsorbed to the surface of the particles have a molecular weight that is at least about 55%, such as at least about 75% of the average molecular weight of the all of the molecules absorbed to the surface.

Because of the above features regarding narrow size distribution and narrow size dispersity, the colloids are homogenous or uniform with respect to the polymer-coated particles thereof.

The density of the colloids may vary, but in representative embodiments ranges is at least about 1.01, such as at least about 1.05, and may be as high as 1.30 or higher, where the density may range from about 1.07 to about 1.10, such as from about 1.085 to about 1.095, as compared to the density of water at 20° C.

The concentration of particles in the liquid medium in the subject colloids may vary, but ranges in certain embodiments from about $1\times10^{10}$ to about $1\times10^{15}$ particles/ml, such as from about $1\times10^{11}$ to about $5\times10^{11}$ particles/ml, including from about $2\times10^{11}$ to about $3.75\times10^{11}$ particles per ml.

In certain embodiments, the metal and conductive polymer components are matched with respect to an optical parameter, such as absorbance. In representative embodiments, the metal and conductive polymer components are ones that, when measured separately using the protocol described below in the experimental section below, have an absorbance maximum that differs by less than about 50 nm, such as by less than about 40 nm, including by less than about 25 nm. The "common" absorbance maximum (i.e., the average of the two individual absorbance maxima) may vary, ranging from about 1 to about 10, such as from about 3 to about 4. Representative matched metal/conductive polymer pairings of interest include, but are not limited to: gold/polyanilines (e.g., gold/poly(aniline-2-carboxylic acid); silver/poly(thiophene-3-carboxylic acid); and the like.

In certain embodiments, the composite colloid is more sensitive to changes in refractive index of the liquid medium in which the particles are suspended as compared to a control colloid that is made up of metal particles not coated with the conductive polymer. By more sensitive is meant at least about 10 fold more sensitive, such as at least about 100 fold more sensitive, including at least about 1,000 fold more sensitive, compared to a control, as determined using the assay reported in the Experimental Section, below.

In certain embodiments, the particles display a ligand, e.g., that specifically binds to an analyte of interest, a therapeutic moiety, etc., on their surface. By display is meant that the ligand is immobilized on the surface of the particle, where the ligand may be covalently or non-covalently bound to the surface of the particle. The density of ligand on the particle surface may vary, but may range from about 2 to about 50, such as from about 5 to about 25 molecules per particle.

As indicated above, a variety of different types of ligands may be displayed on the surface of the particles of the colloids. In certain embodiments, the particular ligand that is present depends on the nature of the analyte that is to be bound by the ligand in a given application, such as the analyte detection applications discussed below. Representative ligands of interest include, but are not limited the ligands discussed above, such as nucleic acids, peptides, etc.

The pH of the colloid may vary, and in representative embodiments ranges from about 2 to about 12, such as from about 4.5 to about 9.0. The colloids may include a number of different additional components apart from the polymer coated metal particles, where additional components of interest include, but are not limited to: salts, buffering agents, detergents, stabilizers, and the like.

In certain representative embodiments, the colloid is substantially free of non-adsorbed polymer, i.e., the liquid component of the colloid has little, if any, free polymer present therein. As such, the concentration of free polymer in solution in the liquid medium of the colloid, if present at all, does not exceed about 5%, and more particularly does not exceed about 1% of the quantity used.

Methods of Fabrication

The subject colloids may be prepare using any convenient protocol that results in the production of a colloid of the invention, e.g., as described above. In a representative embodiment, an initial or precursor metal colloid and a water-soluble conductive polymer are combined with each other in a manner sufficient for the water-soluble conductive polymer to adsorb to the surface of particles of the metal colloid and thereby produce the product composite colloid of the invention.

In representative embodiments, a first volume of a metal colloid is combined with a second volume of a solution of the water-soluble polymer. The ratio of the volumes of colloid to polymer solution may vary, but in certain embodiments ranges from about 100 to about 1, such as from about 50 to about 20, including from about 10 to about 5. In certain embodiments, the colloid and solution polymer are combined by introducing the volume of colloid into the polymer solution. In other embodiments, the colloid and solution polymer are combined by introducing the volume of polymer solution into the colloid. In certain embodiments, combination of the volumes occurs with agitation, e.g., by stirring one of the fluids while the other is added to it, by combining the volumes while moving, e.g., shaking, the container in which they are combined, etc.

The metal colloid that is combined with the water-soluble polymer is, in representative embodiments, a metal colloid of a noble metal suspended in an aqueous liquid medium. In representative embodiments, the colloid is uniform with respect to the nature of the metal particles, where the particles have an average diameter ranging from about 2 nm to about 1 µm, such as from about 3 nm to about 60 nm, including from about 5 nm to about 30 nm and a narrow size distribution, as described above. In representative embodiments, the density of the particles in the medium ranges from about 1.01 to about 1.30, such as from about 1.02 to about 1.10. In certain embodiments, the pH of the colloid is chosen to ensure that the metal particles of the colloid have a negatively charged surface, where the pH may range from about 2 to about 12, including from about 1 to about 10, such as from about 3 to about 5.

The water-soluble polymer solution is, in representative embodiments, a solution of a water soluble conducting polymer, as described above, where the concentration of polymer in the solution may range from about 0.02 to about 2 g/100 ml, such as from about 0.02 to about 0.5 g/100 ml, including from about 0.2 to about 0.3 g/100 ml. The average molecular weight of the polymer ranges, in representative embodiments, from about 1,500 Da to about 32,000 Da, such as from about 5,000 Da to about 7,000 Da, and has a narrow size dispersity, where at least about 55%, such as at least about 75% of the polymers present in the solution have a molecular weight that is at least about 90 to about 110%, such as at least 95 to about 105% of the average molecular weight. In certain embodiments, he pH of the water-soluble polymer solution is chosen so that the water-soluble polymers are positively charged, where the pH may range in representative embodiments from about 2 to about 7, such as from about 3 to about 5.

In certain embodiments, the volumes of the metal colloid and water soluble polymer solution, as well as parameters thereof (e.g., density, pH, concentration, etc.) that are combined in this step of the subject invention are ones that have been predetermined to result in the production the product composite colloid that is stable and substantially free of solution phase polymer, where by "substantially free is meant that the concentration of solution phase polymer is less than about 5%, such as less than about 1%. A feature of these embodiments is that this product colloid is produced without any washing or other step that removes solution phase polymer from the colloid. The appropriate volumes and parameters thereof for practicing these embodiments of the subject methods may be determined using the protocols discussed in the experimental section, below.

In combining the metal colloid and the water-soluble polymer, the two components are combined into a reaction mixture, and the resultant reaction mixture maintained for a period of time sufficient for the desired colloid to be produced. Generally, the reaction mixture is maintained at a temperature ranging from about 15° C. to about 30° C., e.g., from about 18° C. to about 22° C., for a period of time ranging from about 5 minutes to about 60 minutes, such as from about 10 minutes to about 20 minutes.

In certain embodiments, the methods may further include a step of modifying the surface of the composite particles of the colloid to display a ligand, e.g., that specifically binds to an analyte of interest. Where desired, a ligand may be immobilized directly or indirectly, e.g., via a linking group, on a surface of the particles using any convenient protocol, including one that employs covalent bonding or non-covalent bonding of the ligand to the particle, e.g., either to the metal component directly or to the polymer present on a surface of the particle, e.g., via reaction with a functional group present on the polymer. The ligand may be any of a number of different types of molecules, e.g., nucleic acid, peptide, organic and inorganic small molecules, etc., as reviewed above. As indicated above, where desired the reaction mixture may be agitated.

Utility

The subject colloids, as described above, may be employed in a variety of different applications. For example, the subject colloids may be used to screen a sample for the presence or absence of one or more target analytes in the sample. As such, the invention provides methods of detecting the presence of one or more target analytes in a sample.

In such applications, a volume of colloid, e.g., one that includes a ligand specific for the analyte, is contacted with the sample to be screened, and an optical parameter of the colloid is monitored to detect a change therein, e.g., a change in absorption of the colloid at a given wavelength. Any convenient optical parameter may be assessed or monitored in this step, where representative parameters include, but are not limited to: absorption, scattering, fluorescence, luminescence and the like. The optical parameter may be monitored using any convenient device and protocol, where suitable protocols are well known to those in the art and representative protocols are described in greater detail in the experimental section, below. The presence or absence of a change in the optical parameter is then used to make a determination of whether or not the analyte of interest is present in the sample.

In the broadest sense, the methods may be qualitative or quantitative. As such, where detection is qualitative, the methods provide a reading or evaluation, e.g., assessment, of whether or not the target analyte is present in the sample being assayed. In yet other embodiments, the methods provide a quantitative detection of whether the target analyte is present in the sample being assayed, i.e., an evaluation or assessment of the actual amount of the target analyte in the sample being assayed. In such embodiments, the quantitative detection may be absolute or, if the method is a method of detecting two or more different target analytes in a sample, relative. As such, the term "quantifying" when used in the context of quantifying a target analyte(s) in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

The subject methods can be employed to detect the presence of one or more target analytes in a variety of different types of samples, including complex samples having large amounts of non-target entities, where the subject methods provide for detection of the target analytes(s) with high sensitivity. As such, the subject methods are highly sensitive methods of detecting one or more target analytes in a simple or complex sample. The sample that is assayed in the subject methods is, in certain embodiments, from a physiological source. The physiological source may be eukaryotic or prokaryotic, with physiological sources of interest including sources derived from single celled organisms such as bacteria and yeast and multicellular organisms, including plants and animals, particularly mammals, where the physiological sources from multicellular organisms may be derived from particular organs or tissues of the multicellular organism, or from isolated cells or subcellular/extracellular fractions derived therefrom.

The methods of the present invention may be used to detect a wide variety of analytes. Analytes of interest may be present as liquids, solids or gases (e.g., organophosphates, etc.). Analytes of interest can be a proteinacious molecules, such as, but not limited to, proteinacious analytes, including peptides and proteins and fragments thereof, as well as prions and other proteinaceous types of analytes, where the analytes may be a single molecule, a complex that includes two or more molecular subunits, which may or may not be covalently bound to each other, a microorganism, e.g., virus or single celled pathogen, a cell, a multicellular organism or portion thereof, and the like.

In addition, the subject methods may also be used to screen for compounds that modulate the interaction of a given specific binding member pair. The term modulating includes both decreasing (e.g., inhibiting) and enhancing the interaction between the two molecules. For example, where the colloid displays a first member of a binding pair and the colloid is contacted with the second member in the presence of a candidate agent, the effect of the candidate agent on the interaction of the binding member pairs can be evaluated or assessed.

A variety of different candidate agents may be screened by the above methods. Candidate agents encompass numerous chemical classes, though typically they are organic molecules, preferably small organic compounds having a molecular weight of more than 50 and less than about 2,500 Dolton. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in a variety of methods, including methods of modulating the activity of the target analyte, and conditions related to the presence and/or activity thereof.

Additional applications of the subject colloids include therapeutic applications, e.g., as drug delivery vehicles. For example, a therapeutic agent can be displayed on a surface of the nanoparticles, and an effective amount of the colloid that is made up of the nanoparticles administered to a subject to treat the subject. Where desired, nanoparticles of the colloid may be further modified to include a targeting moiety, e.g., to direct the nanoparticles to a desired location.

Kits & Systems

As summarized above, also provided are kits and systems for use in practicing the subject methods. The kits and systems at least include the subject colloids or components thereof, as described above. The kits and systems may also include a number of optional components that find use in the subject methods. Optional components of interest include buffers, and the like.

In certain embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

Experimental

The following describes a process for the production of poly(aniline)-colloidal gold nanoparticles and reports the opto-electronic characterization of the material synthesized.

I. Synthesis

A. Synthesis of Water-Soluble Poly(aniline-2-carboxylic acid) (PANI-COOH).

The synthesis consists in oxidizing the monomer in aqueous solution with iron chloride and the detailed procedure has been described previously (Englebienne, P., Weiland, M. Water-soluble conductive polymer homogeneous immunoassay (SOPHIA), a novel immunoassay capable of automation. J. Immunol. Methods 1996, 191, 159-170; Englebienne, P., Weiland, M. Synthesis of water-soluble carboxylic and acetic acid-substituted poly(thiophenes) and application of their photochemical properties in homogeneous competitive immunoassays. Chem. Commun., 1996, 1651-1652; Englebienne, P., Indicator reagents for the detection or dosage of an analyte, kits containing them and detection or dosage procedures. Eur. Pat. 0623 822, 1994). Poly(thiophenes) can also be obtained by the same procedure, but the oxidation uses ammonium peroxydisulfate in addition to the iron chloride. At the end of the synthesis, the pH is raised up to 12 with NaOH pellets in order to precipitate the iron chloride as the hydroxide and to decompose the peroxydisulfate. Iron hydroxide is removed by filtration and the polymer solution is used as such. In the present example, the synthetic yield was improved by two means: improved solubilization of the monomer in dimethylformamide:water (1:10) and polymerization under stirring using heat and reflux.

As the gel permeation (GP) chromatographic profile shown in FIG. 1 indicates, the solutions of the polymeric poly(thiophene-3-carboxylic acid) and of PANI-COOH are quite homogeneous with major peaks at a size of approx. 18,000 (20.5 min.) and 6,000 Dolton (24 min.), respectively and minor peaks with a size of approx. 25,000 (19 min.) and 15,000 Dolton (21 min.), respectively. Such sizes correspond to oligomers made of 45 and 110 repeats for PANI-COOH, respectively. Please note that these values are not absolute values because the column has been calibrated with globular proteins and the polymers are not necessarily globular in shape.

Chromatographic conditions:

HPLC column: TSK 2000 SW, 7.5×600 mm.

Elution: 50 mM phosphate pH 7.4.

Flow rate: 1 ml/min.

Injection: 50 µl.

Detection: O.D. 254 nm, 0.5 AUFS.

Paper speed: 1 mm/min

B. Synthesis of Colloidal Gold Nanoparticles.

The nanoparticles are obtained by reduction of a boiling hydrogen tetrachloroaurate solution by sodium citrate. The process is well-known and is described in the following publication (Englebienne, P., Van Hoonacker, A., Verhas, M. High throughput screening using the surface plasmon resonance effect of colloidal gold. Analyst, 2001, 126, 1645-1651). Detailed procedures are provided in the book referenced to above to obtain nanoparticles of various sizes. The nanoparticles used in the present report have an approximate diameter of 50 nm and are homeodisperse.

C. Synthesis of Composite Poly(aniline-2-carboxylate)-Colloidal Gold Nanoparticles.

Colloidal noble metal nanoparticles are negatively charged over a wide range of pH. Procedures designed for coating such nanoparticles with proteins take advantage of this property. The nanoparticles are mixed with the protein at a pH below the protein pI and the protein adsorbs on the particle surface by charge interaction. Such protein-coated particles are stable and do not flocculate in the presence of high salt concentrations. Common procedures involve the addition of proteins in excess to the gold so as to avoid the formation of bridges between individual nanoparticles, made by protein molecules. After protein adsorption, the nanoparticles are centrifuged and washed so as to remove the excess protein. The colloid is then resuspended in a suitable buffer. During the previous years, we have developed a process that simplifies tremendously that procedure, which is described in our book and our J. Mater. Chem. Publication referenced to above. The principle consists in mixing the gold colloid in test tubes with increasing protein concentrations at a suitable pH. After mixing, a 1 M NaCl solution is added. In tubes were the particles are not completely stabilized with a protein layer, the nanoparticles flocculate, which induces a strong red-shift in their visible absorption spectrum, from the native surface plasmon resonance (SPR) peak of 520 nm (for gold) up to 600-800 nm, resulting in a decrease in O.D. at the SPR peak. A binding isotherm constructed from the spectrum data and protein concentrations added to the gold colloid therefore allows to determine the minimal protein concentration required to fully stabilize the gold sol, in other words, the protein concentration required for coating single nanoparticles with a complete protein layer. The process is then scaled-up for the production of larger volumes.

In the present case, we reasoned that a water-soluble conductive polymer substituted by ionizable groups along the backbone could behave exactly in the same way. For PANI-COOH for instance, we considered that at low pH, all the carboxylic groups would be protonated and would therefore be capable of coating colloidal gold nanoparticles by charge adsorption, producing stable colloidal composites. In order to test the hypothesis, we first examined the effect of the pH to the possible capacity of PANI-COOH to stabilize colloidal gold nanoparticles.

The protocol used was as follows. To a series of plastic tubes containing 0.01 ml of the PANI-COOH solution, 1 ml of the colloidal gold solution was rapidly injected with a positive displacement pipette and the tube immediately vortex-mixed. The colloidal gold solution added to each independent tube was adjusted to various pH values using either 10 mM sodium carbonate or 300 mM HCl solutions, respectively. Then, 0.5 ml of a 1 M solution of sodium chloride was added to each tube which was further vortex mixed, so as to flocculate the particles that were not stabilized. UV-vis. spectra were recorded for each solution. The peak wavelength and absorbancy at the maximal (SPR) wavelength were recorded and plotted versus pH. The results are shown in the FIG. 2.

Figure 2:
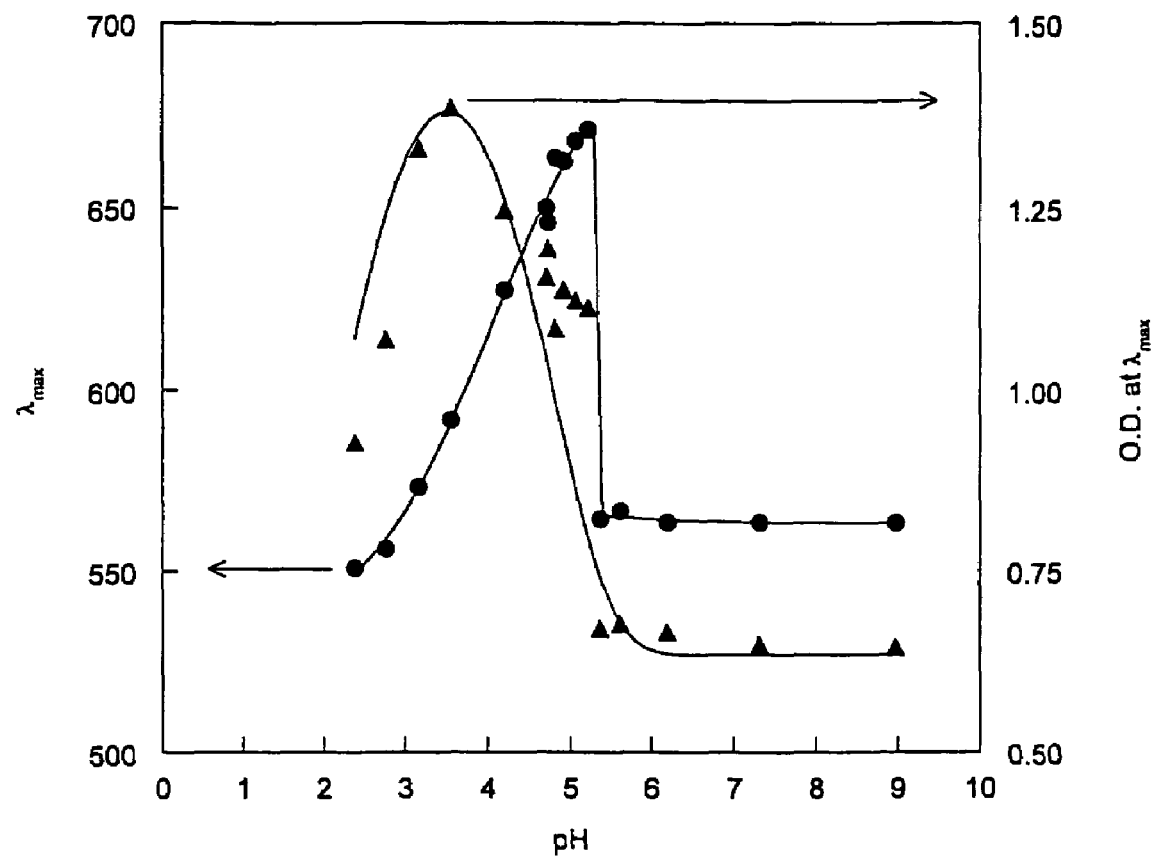
FIG. 2. Stabilization of colloidal gold nanoparticles toward salt flocculation by PANI-COOH at different pH values.

As shown on FIG. 2, the SPR peak wavelength of the gold colloid shifts progressively to the red from 550 to 660 nm from pH 2 to 5 and then drops rapidly back to 560 nm above pH 5. The O.D. at the peak shows a maximum around pH 3 and falls rapidly to the half above pH 5. The low O.D. at the SPR peak above pH 5 indicates that the flocculation is such that most of the particles precipitate at the bottom of the cuvette. The stable maximal wavelength and O.D. observed correspond to the soluble PANI-COOH remaining in the supernatant. Below pH 5, the particles are likely to be stabilized with an optimum close to pH 3. This first experiment led us to conclude that water-soluble PANI-COOH could stabilize the gold nanoparticles, even if the concentration was not optimal. Interestingly enough, these results are moreover in line with the ionization data available for the monomer which displays two pKa values of respectively 2.10 and 4.94 (Handbook of Chemistry and Physics, CRC Press). Thus, around the first pKa value, the molecules is protonated and capable of stabilizing the gold particles by charge adsorption, although above the second pKa value, the repulsion due to negative charges of both gold and PANI-COOH allows the salt added to bridge and flocculate the particles.

Figure 3:
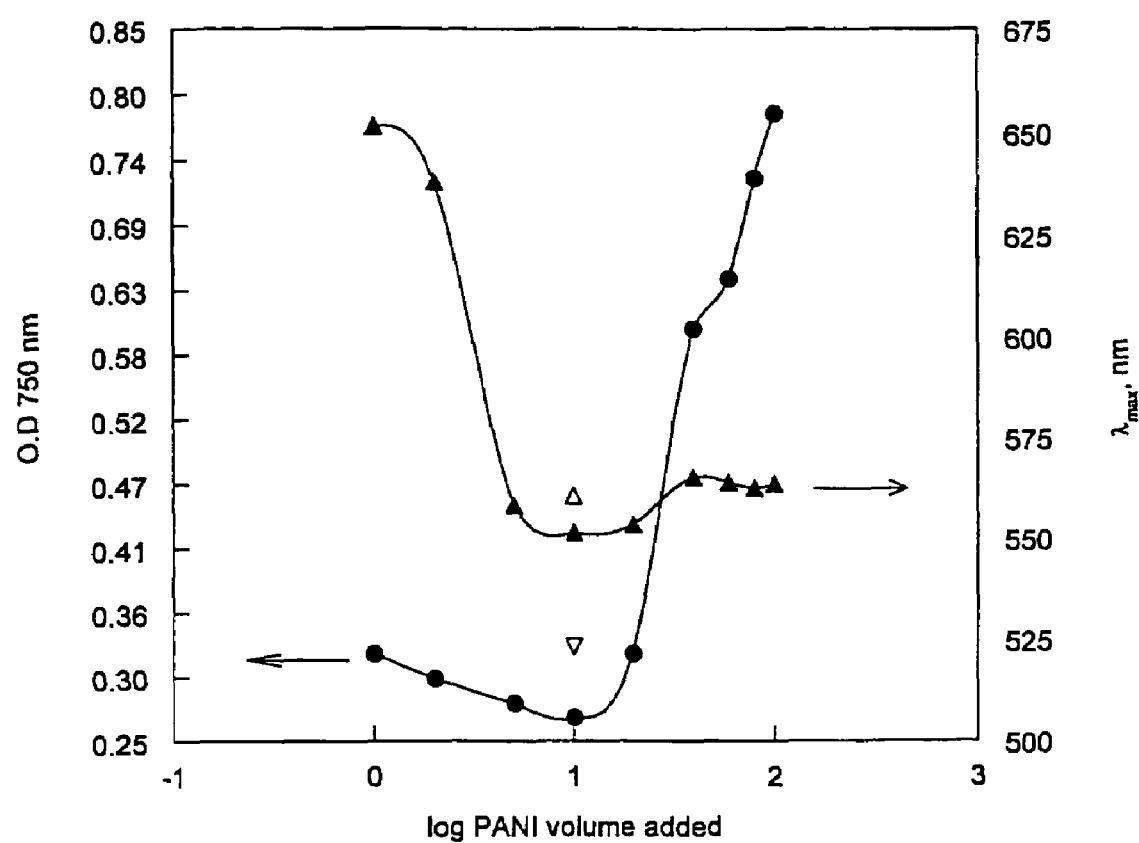
FIG. 3. Stabilization of colloidal gold nanoparticles toward flocculation by salt by increasing concentrations of PANI-COOH at fixed pH. Original absorption wavelengths of PANI-COOH and gold nanoparticles are respectively shown by up and down open triangles.

Once the optimal pH for stabilizing the particles determined, it was necessary to determine the minimal PANI-COOH concentration required for stabilizing the particles. For this optimization, the following protocol was used. Increasing volumes of the PANI-COOH solution (from 0.001 up to 0.1 ml) were added to individual plastic tubes. The volume was adjusted to 0.1 ml in each tube by the addition of appropriate volumes of distilled water. After mixing, 1 ml of colloidal gold solution of which the pH was adjusted to 2.38 using HCl 300 mM, was rapidly injected in each individual tube using a positive displacement pipette and each tube was immediately vortex mixed. Then, 0.5 ml of a 1 M solution of sodium chloride was added to each tube which was further vortex mixed, so as to flocculate the particles that were not stabilized. UV-vis. spectra were recorded for each solution. The maximal wavelength of absorbance was recorded, along with the optical density (O.D.) at 750 nm which is representative of the flocculation of the colloid. Results are displayed in the graph of (FIG. 3.). The maximal wavelengths of absorption of the gold and PANI-COOH solutions are respectively shown by down and up open triangles on the FIG.

Figure 4:
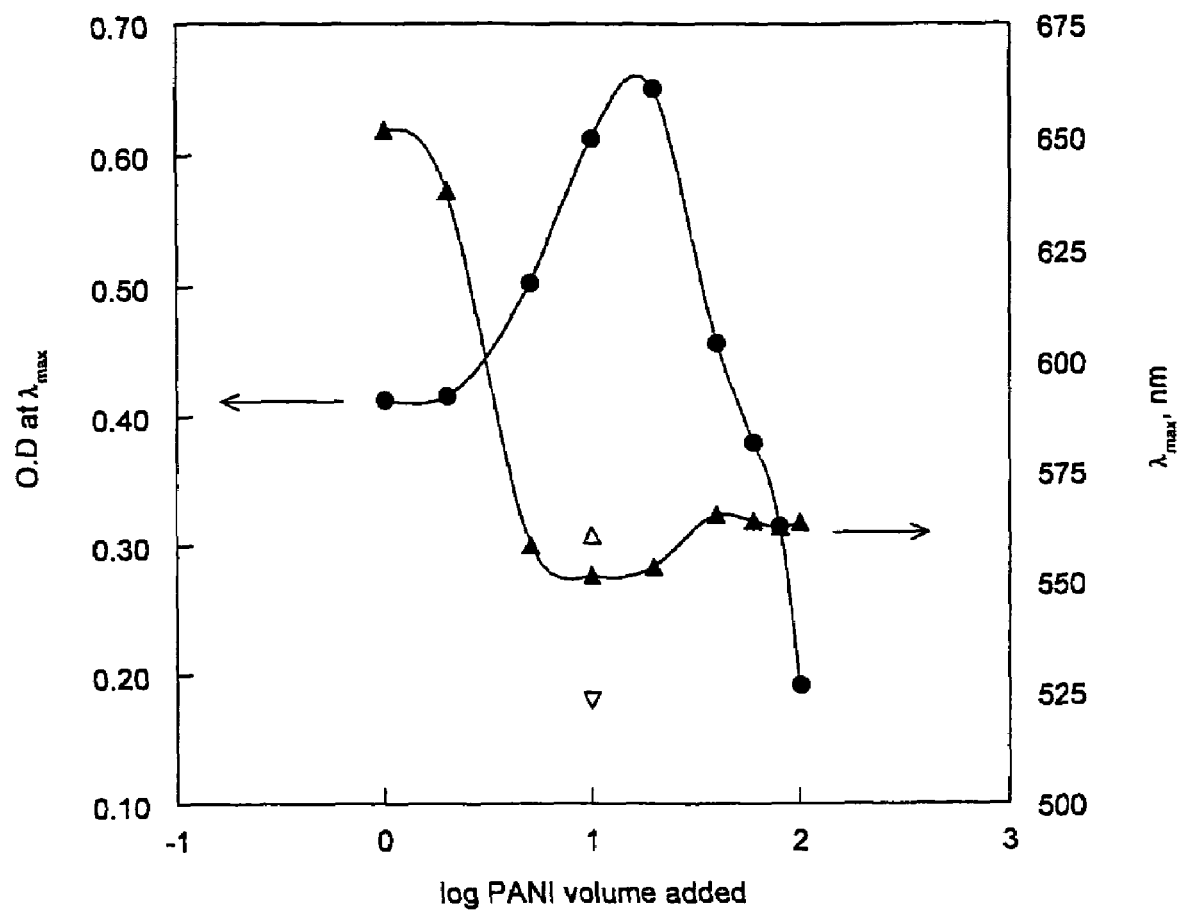
FIG. 4. Progressive stabilization of gold nanoparticles toward flocculation by salt by increasing concentrations of PANI-COOH at fixed pH, as measured by the O.D. at the maximal wavelength after salt addition.

The data shown in FIG. 3. indicate that the gold particles were stabilized after incubation with 0.01-0.02 ml of PANI-COOH per ml of sol (minimal wavelength and O.D. 750 nm). These conclusions are further confirmed by the data shown in FIG. 4. Here, the O.D. at the SPR peak is plotted, along with the peak wavelength versus the log volume of PANI-COOH solution added. Because increasing volumes of PANI-COOH were added to the gold and given the fact that PANI-COOH absorbs at a wavelength close to that of the gold colloid (560 nm), the contribution of PANI-COOH in the O.D. at the SPR wavelength for each volume was subtracted from the data plotted. As shown by the figure, the maximal O.D. at the SPR peak of gold is observed for PANI-COOH volumes added of 0.01-0.02 ml.

With these optimization data in hand, the procedure was scaled-up to higher volumes. A batch of composite material was successfully produced as follows. The PANI-COOH solution synthesized as described above (1.5 ml) was diluted with 8.5 ml distilled water in a beaker containing a magnetic stirrer bar. In a separate vessel, 100 ml of colloidal gold solution synthesized as described above was adjusted under magnetic stirring to pH 2.94 using HCl 300 mM. The PANI-COOH solution was placed on the magnetic stirrer and was mixed at the highest speed. The pH-adjusted gold solution was then added rapidly to the PANI-COOH solution. After mixing, the pH of the mixture was 4.67. The composite sol was further stabilized by the addition of 0.5% Tween 20. The batch was then divided into two equal parts, the first one being buffered with 50 mM sodium acetate at pH 4.95, the other one being buffered with 50 mM sodium borate at pH 9. It is important to note that reversing the order of reagent mixing in the procedure works also.

II. Physico-Chemical Characterization of the Material

A. Preliminary Note.

Figure 5:
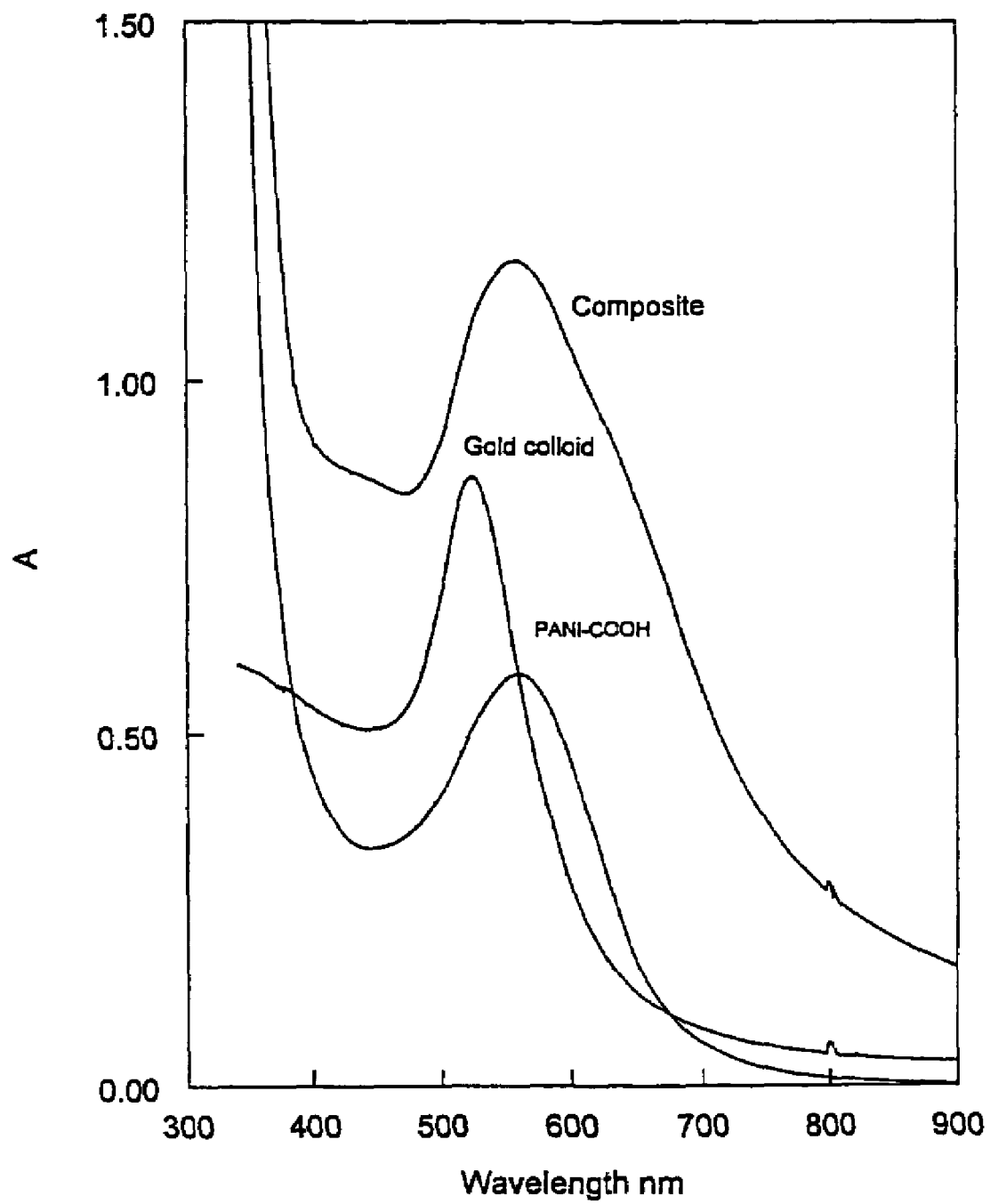
FIG. 5. Visible absorption spectra of solutions of PANI-COOH, colloidal gold nanoparticles and PANI-COOH-gold composite.

Our interest in preparing a composite material made of a conducting polymer and colloidal nanoparticles of noble metal was primarily directed to the possible modifications in the opto-electronic properties of both materials taken individually. The sensitivity of these materials to various changes in their physical environment is transduced by changes in their electronic spectra. Consequently, in order to be able to observe consistant changes in such spectra with the composite materials considered, it was quite reasonable to consider native materials, which, taken individually in their native state, presented similar energies of light absorption. This is the reason why we selected colloidal gold and PANI-COOH. The visible spectrum of gold nanocolloids with particles of 50 nm of diameter suspended in water presents a localized SPR absorption band at 520 nm (see FIG. 5). Consistently, the visible spectrum of a solution of PANI-COOH in water presents an absorption band at 560 nm. The visible spectra of the original gold, PANI-COOH and of the composite material obtained by their combination are presented in FIG. 5. As expected, the characteristics of the composite material spectrum result from the addition of those of the original materials used for its production.

B. Stability.

Figure 6:
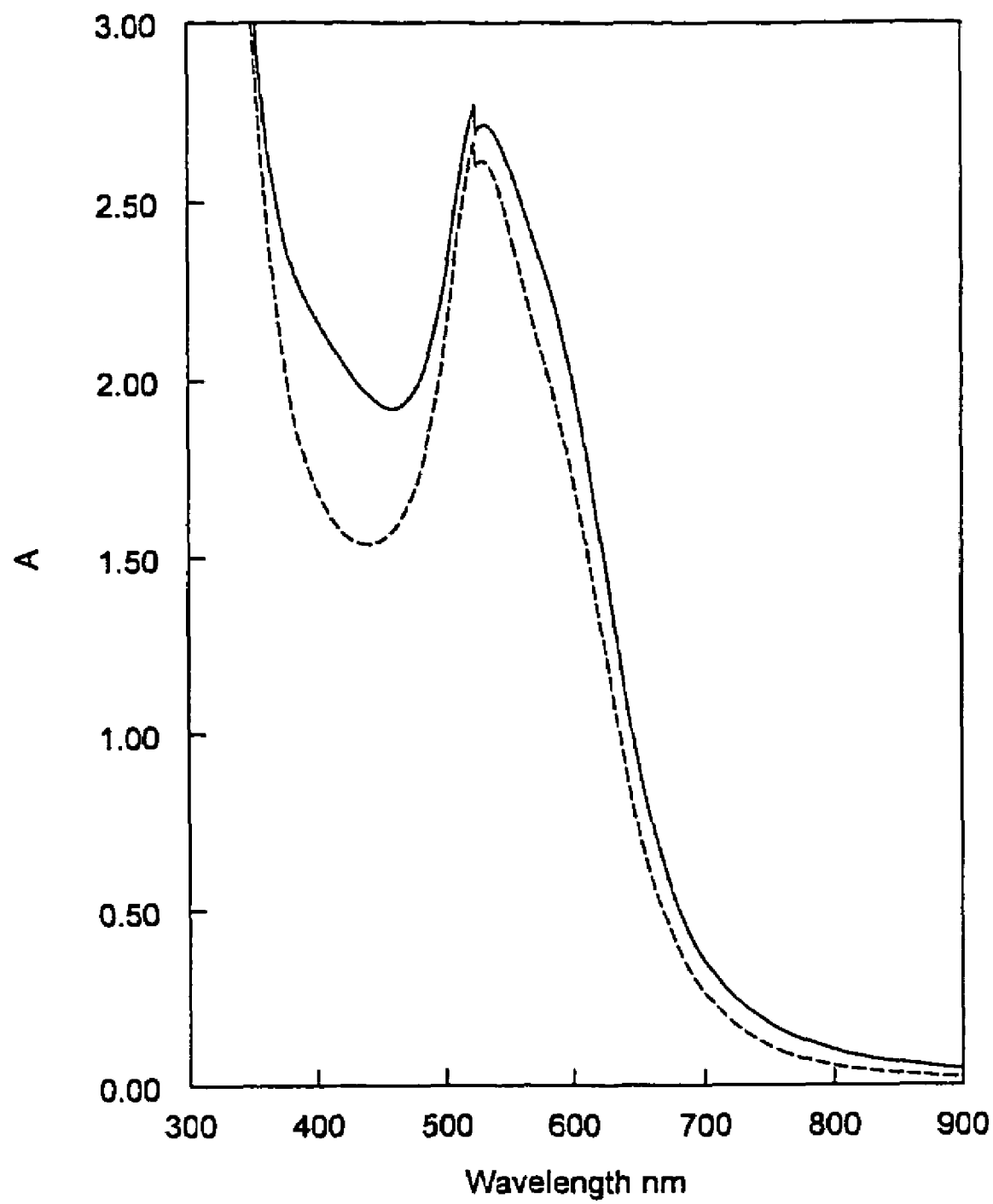
FIG. 6. Absorption spectra of the composite material buffered at pH 9 taken immediately after synthesis (solid line) and after three and a half months of storage at room temperature (dashed line).

FIG. 6. compares the visible absorption spectra of the composite material taken after synthesis and more than 3 months later. The maximal absorption wavelength is identical and no significant loss of absorbance at this wavelength can be observed. The composite is likely to have matured during storage as the absorption peak is more homogeneous in the spectrum taken at the later date.

Additionally, over a period of more than 3 months after the production, no sedimentation has been observed. The composite material, whether at acidic or basic pH is a stable colloidal solution. In that regard, it appears to the naked eye essentially indistinguishable from controls solutions of colloidal gold and PANI-COOH compared under the same conditions of concentration of materials and pH.

C. Reactivity Toward Oxido-Reduction.

C.1. Sensitivity to pH.

Figure 7:
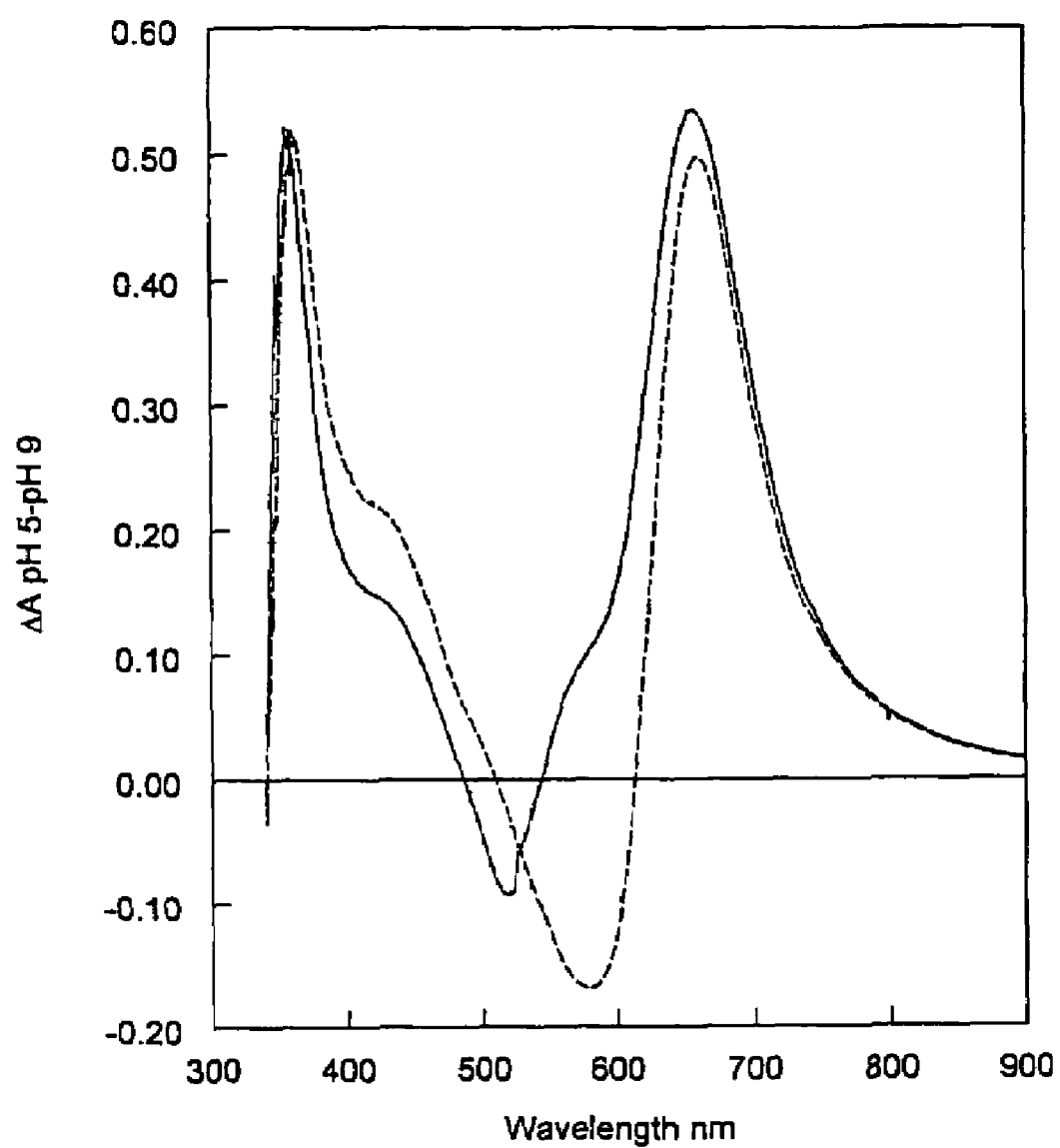
FIG. 7. Difference spectra between pH 4.95 and pH 9 of the composite material (solid line) and of the PANI-COOH solution (dashed line).

It is well known that conducting polymers are sensitive to pH changes. This is particularly true for poly(aniline) which changes its electronic structure with pH. The progressive p-doping (oxidation) by protonation of the non-conducting leucoemeraldine into the conducting emeraldine results in a shift from the absorption of high energy photons (343 nm, 3.61 eV) to the absorption of both higher (330 nm, 3.75 eV) and lower (637 nm, 1.94 eV) photons. Further oxidation leads to the fully quinonoid form pernigraniline which is insulating. A solution of PANI-COOH behaves similarly towards light when progressively protonated (see e.g. Englebienne, P. Synthetic materials capable of reporting biomolecular recognition events by chromic transition. *J. Mater. Chem.*, 1999, 9, 1043-1054). Therefore, it was interesting in the first instance to verify if the composite material was still capable of reporting the structural changes occurring in the structure of the polymer by protonation by similar changes in its UV-vis. spectrum. To this aim, we compared the electronic spectra of the composite buffered at pH 4.95 with the solution buffered at pH 9. For comparison, we prepared buffered solutions of PANI-COOH at the concentration used to prepare the composite and we adjusted the pH at the same respective values. When comparing the spectra of the two materials at the respective pHs, we observed indeed the expected changes. The shifts in wavelength were identical for the conducting polymer and the composite, and the importance of the changes in absorbance were similar in both the composite and plain polymer. In order to illustrate these changes, we recorded the difference spectrum between the materials adjusted at pH 4.95 and the materials at pH 9 (reference cell). These difference spectra are presented in FIG. 7. The appearance of the new bands in the protonated materials at both high (380 and 420 nm) and low (680 nm) energy photons are identical for the composite (solid line) and the native conducting polymer (dashed line). The negative peak at 580 nm in the polymer is shifted to shorter wavelengths in the composite i.e. in the region of the SPR peak of gold. This results probably from changes in the energy of the conduction electrons at the metal surface.

C.2. Response to Reduction.

Another interesting feature of water soluble PANI-COOH, which is also shared with insoluble poly(aniline), is the photonic sensitivity of the material to oxidoreuction. Both protonation and changes in oxidation states of the emeraldine salts give rise to marked transitions in the optical spectrum (Grummt, U.-W., et al. *Anal Chim. Acta* 1997, 547, 253). That property was recently applied in a highly sensitive assay for ascorbic acid, using a poly(aniline) film deposited in microtiter plates (Bosi, A., et al., *Anal. Chem.* 2000, 72, 4296). When compared to currently available analytical techniques, this new assay presents several marked advantages because it uses smaller sample volumes, displays a lower detection limit, and proves reproducible in an extended range of analyte concentrations.

In order to compare the redox sensitivity of the composite nanomaterial to the of PANI-COOH, we incubated at different pH values both materials with increasing concentrations of ascorbic acid (0.9-500 mg/l) and recorded the difference spectra versus the mixture devoid of reductant. Whatever the pH, both materials reported their reduction by a progressive decrease in absorbance at 600 nm. In agreement with previously reported results for the microtiter plate assay, we observed the strongest changes in the 600 nm absorbance intensity for both materials at pH values below 4. The composite nanomaterial displayed, however, a stronger optical reactivity to reduction than water-soluble PANI-COOH.

Figure 8:
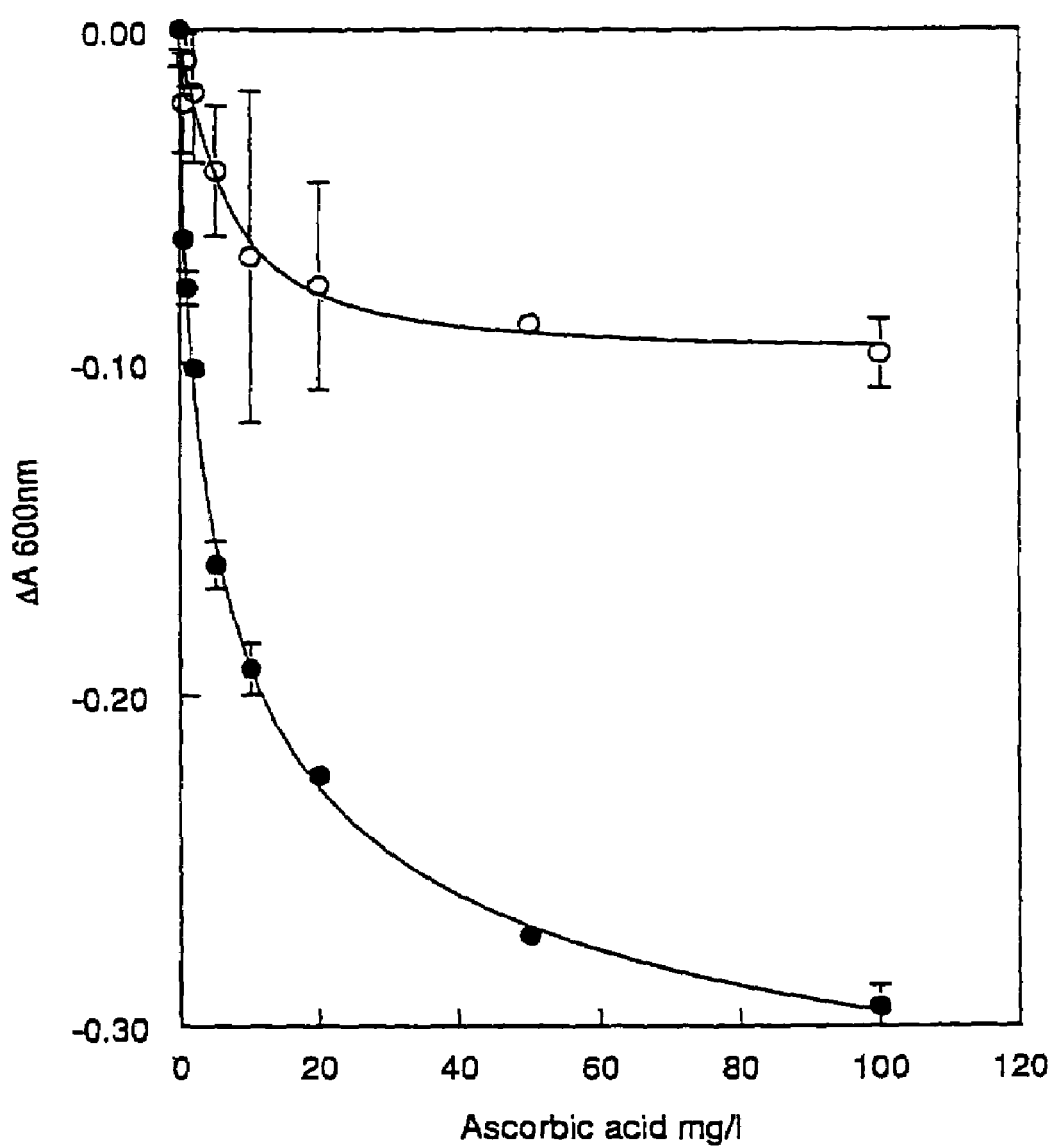
FIG. 8. Dose-response curves observed respectively with PANI-COOH (open circles) or colloidal nanocomposite (closed circles) solutions after reaction with increasing does of ascorbic acid. Data are averages±S.D. of triplicate measurements.

With an aim to further document the difference, we designed a simple assay for ascorbic acid in solution based on the previously described procedure, using the reagents in aqueous solution rather than as a solid film. In the presence of ascorbic acid, the reproducibility of the optical measurements was rather poor with PANI-COOH, as can be see by the error bars for that dose-response curve, shown in FIG. 8 (upper curve). This is most likely due to the progressive loss of solubility of PANI-COOH at low pH values. In contrast, the optical response of the composite nanomaterial to reduction with ascorbic acid was highly reproducible and the dose-response curve was must steeper, as shown in FIG. 8 (lower curve). With PANI-COOH, the absorbance change for a 20 mg.l ascorbic acid dose (0.076 AU) was comparable to that observed in the microtiter plate assay (0.118 AU) [20]. For the same analyte dose, the response for the composite nanomaterial was, however, much higher (0.22 AU). We further compared the least detectable doses (LDD), which were measure at three times the standard deviation of the zero response of each system. The calculated LDD was 3.39 mg/l for the PANI-COOH assay, which was close to the detection limit of the previously reported microtiter plate assay. Comparatively, the composite nanomaterial was 60 times more sensitive, with a LDD calculated at 0.057 mg/l.

Such high sensitivity with good reproducibility and linearity in solution makes the composite nanomaterial an excellent biosensing reagent requiring a level of redox sensitivity at the lower micromolar range. Some examples of applications in which the composite nanomaterial finds use include the plasmatic antioxidant capacity and the detection and quantitation of superoxide radicals in cells.

D. Reactivity Towards the Refractive Index of the Medium.

The localized SPR peak of a colloidal gold nanoparticle solution is exquisitely sensitive to changes in the refractive index of the medium that surround them. The sensitivity is such that we use this property to measure biomolecular interactions occurring at the surface of particles coated with antibodies or receptors (Englebienne, P., Van Hoonacker, A., Verhas, M. Surface plasmon resonance: Principles, methods and applications in the biomedical sciences. *Spectroscopy*, 2003, 17, 255-273; Englebienne, P., Van Hoonacker, A., Verhas, M., Khlebtsov, N. G. Advances in high throughput screening: Biomolecular interaction monitoring in real-time with colloidal metal nanoparticles *Combin. Chem. High-Throughput Screen.*, 2003, 6, 777-787).

Figure 9:
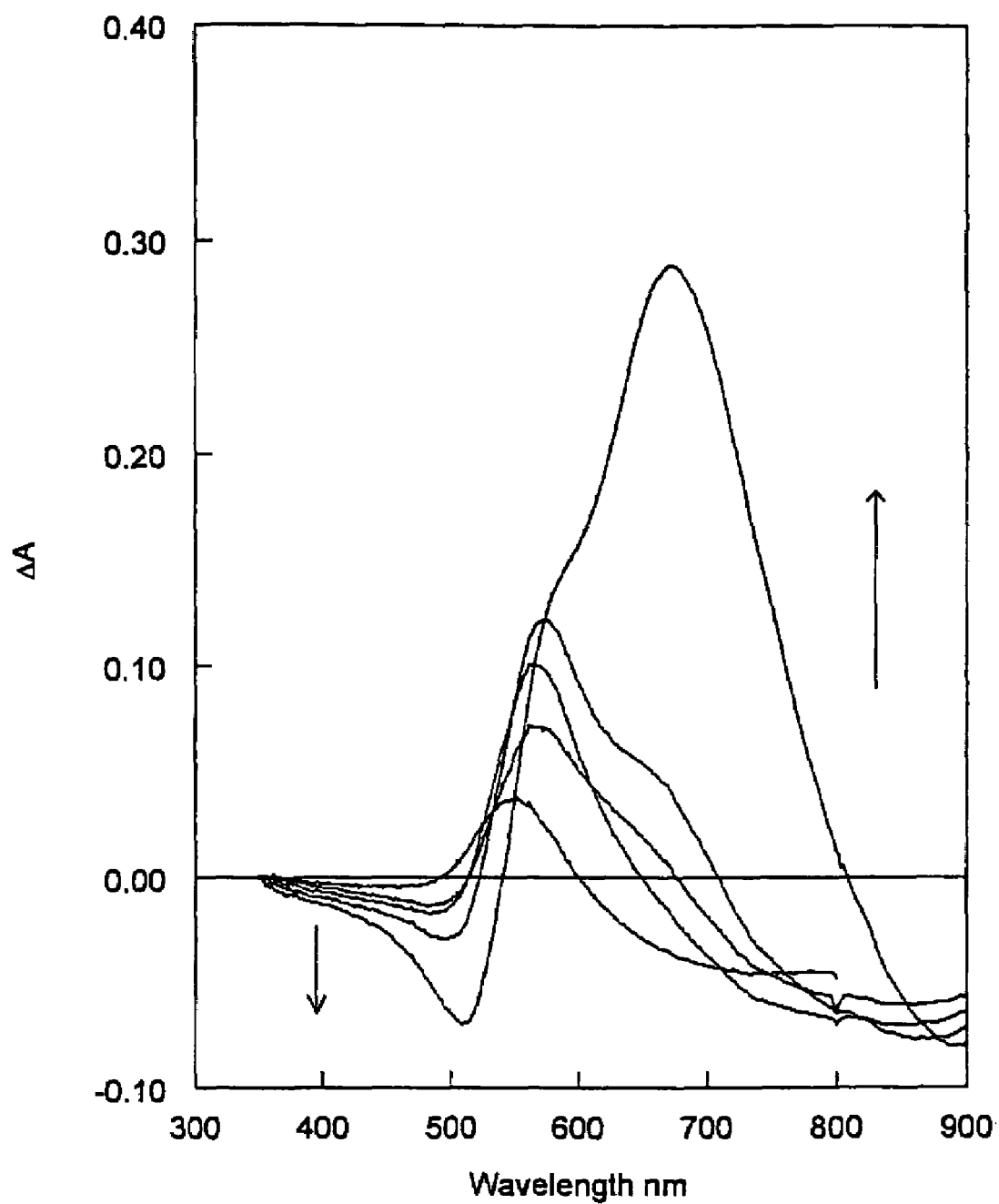
FIG. 9. Effect of glycerol on gold nanocolloids as measured by difference spectroscopy.

We use to test the reactivity of materials toward changes in the refractive index of the medium with glycerol. The colloidal solution (0.5 mL) is mixed with 1.5 mL of aqueous solutions containing respectively 0, 10, 20, 33.3, 50. 66.6 and 100% of glycerol. The final concentrations of glycerol in the medium are thus 0, 7.5, 15, 25, 37.5, 50 and 75%, respectively, which changes the refractive index of the medium from that of water (1.3326) to progressively and respectively 1.3418, 1.3508, 1.3637, 1.3806, 1.3968 and 1.4355. When gold nanoparticles are subjected to such a treatment, the localised SPR peak around 520 nm decreases slightly and the peak is shifted progressively to longer wavelengths, from 550 up to 700 nm. This is exemplified in FIG. 9, which shows the difference spectra of the gold sol in aqueous solutions containing 7.5, 25, 37.5, 50 and 75% of glycerol versus the same colloid in water.

Figure 10:
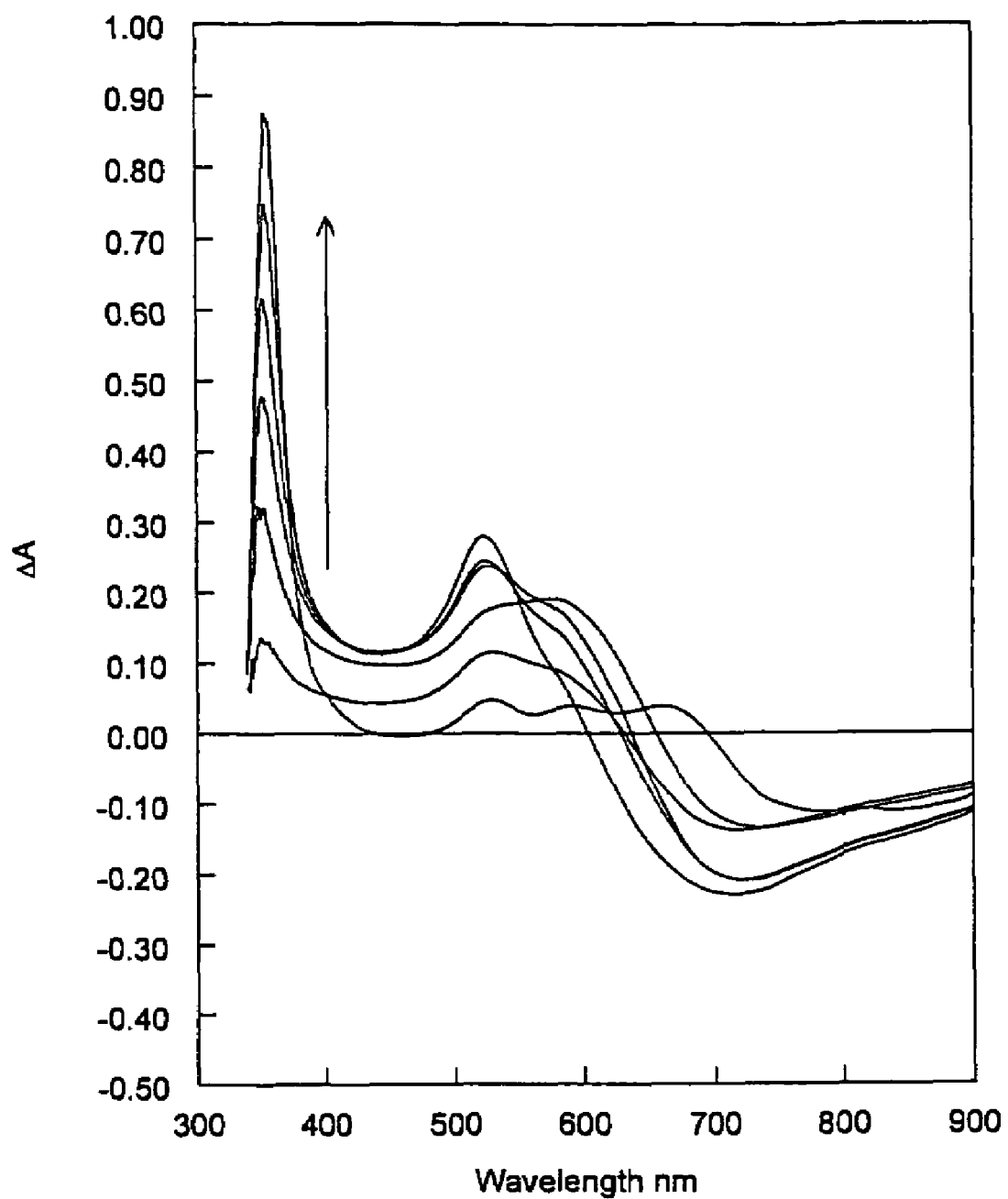
FIG. 10. Effect of glycerol on PANI-COOH-gold composite nanocolloids as measured by difference spectroscopy.

Because in the composite, the gold nanoparticles are covered with a layer of conductive polymer (PANI-COOH), the opto-electronic behavior of this new material toward the refractive index surrounding the nanoparticles could be modified, or even completely suppressed. Therefore, it was important to check this behavior. The reactivity of the PANI-COOH-gold composite nanoparticles buffered at pH 9 toward changes in refractive index of the medium is exemplified by the difference spectra shown in FIG. 10.

Figure 11:
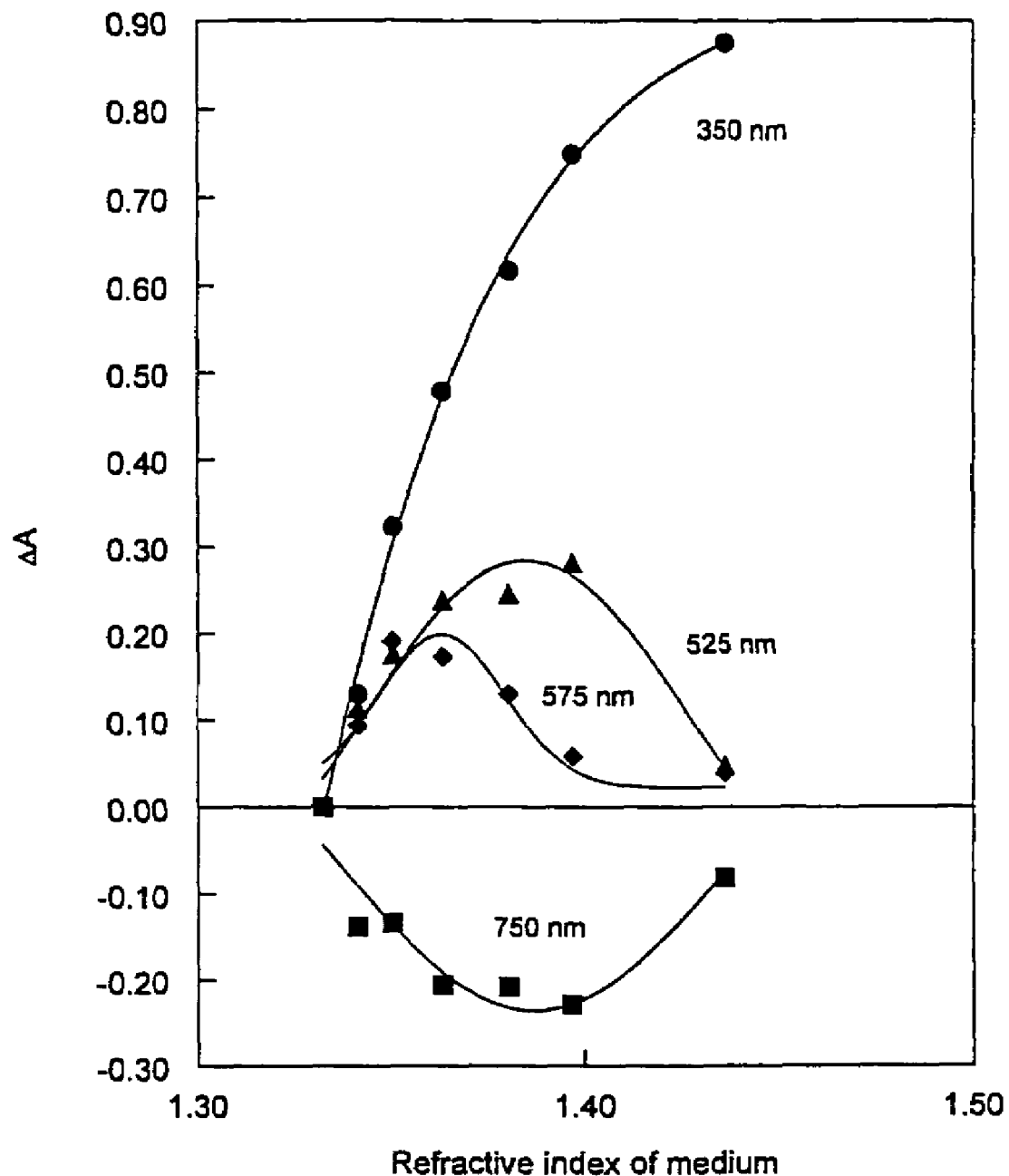
FIG. 11. Evolution of absorbances at typical wavelengths of PANI-COOH-gold composite nanoparticles as a function of changes in the refractive index of the medium.

Interestingly, the progressive localized SPR wavelength shift toward longer wavelengths occurs for low glycerol concentrations, but at higher concentrations, it decreases progressively, whilst a sharp and intense peak appears at a much higher photonic energy excitation (350 nm, 3.54 eV). The variation of absorbance at the typical wavelengths as a function of the changes in refractive index of the medium are shown in FIG. 11.

Typically, the peaks at low energy wavelengths progressively shift to higher energy wavelengths with a consistent and continuous increase in absorbance at 350 nm. Neither gold nanocolloids, nor PANI-COOH solutions present such a behavior in presence of increasing concentrations of glycerol. This new behavior of the composite material most probably results from the conjunction of the high energy electrons of the polymer with the conduction electrons at the gold nanoparticle surface. This creates a cloud of collectively oscillating electrons at the interface with higher energy than that of the conduction electrons of gold. This phenomenon creates a new SPR band in the composite material at shorter wavelengths which absorbs high energy photons to create higher energy photon-plasmon evanescent waves than those that occur in the native gold nanoparticles.

Interestingly, a similar phenomenon has been observed with antibody-coated nanoparticles of gold and silver plated as a monolayer on quartz plates, upon binding of the protein antigen (Frederix, F., Friedt, J. M., Choi, K. H., Laureyn, M., Campitelli, A., Mondelaers, D., Maes, G., Borghs, G. Biosensing based on light absorption of nanoscaled gold and silver nanoparticles. *Anal. Chem.*, 2003, 75, 6894-6900).

Figure 12:
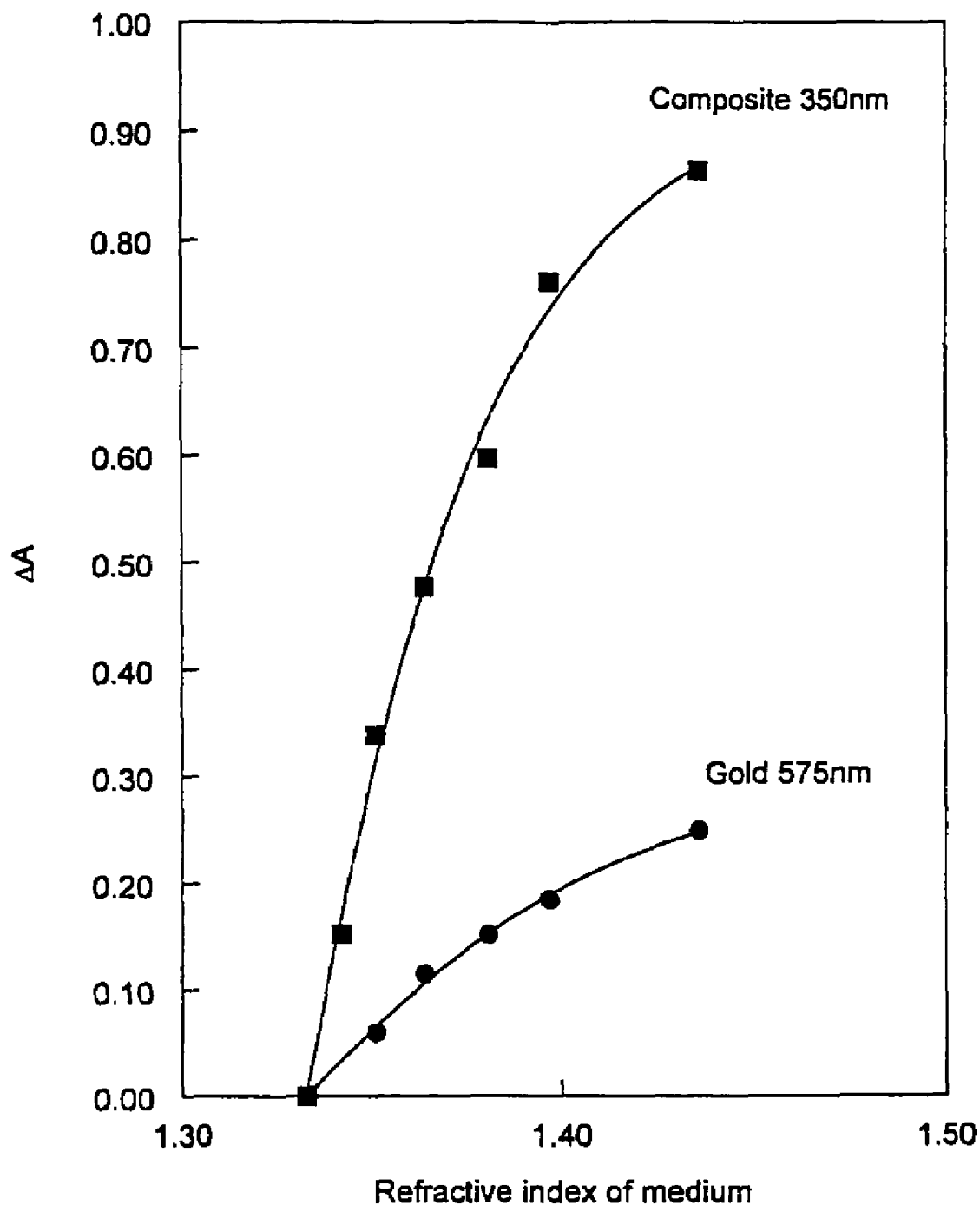
FIG. 12. Comparison of the changes in absorbance at 350 nm for the composite material and changes at 575 nm for gold nanoparticles as a function of the change in refractive index of the medium.

As a consequence of this changed opto-electronic behavior, the measurement of absorbance changes at 350 nm for the composite material is approximately 4 times more sensitive to changes in the refractive index of the medium than the same absorbance changes at 575 nm for gold nanoparticles. This is exemplified in FIG. 12.

It is evident from the above discussion and results that the subject invention provides new materials and methods that are useful in a variety of applications.

The preparation of the composite material consists of mixing the water-soluble conducting polymer at a fixed concentration with the metal nanoparticles at a suitable pH. The composite nanomaterial is stable for months at room temperature in colloidal buffered solutions. The opto-electronic properties of the new composite nanomaterial are sensitive to oxido-reduction and changes in the refractive index of its surrounding medium and their sensitivity is enhanced when compared to the sensitivity of gold nanoparticles and conducting polymer taken separately. The composite nanomaterial presents new opto-electronic properties when compared to those of the separate materials of which it is composed.

As such, use of the subject colloids in analyte detection applications offers an advantage over the sensitive fluorescent dyes or particles in current use because neither conductive polymers nor colloidal metals suffer from photobleaching (i.e., the irreversible photochemical processes leading to non-fluorescent products) or "blinking" effects (i.e. intermittent signal emission due to photoionization) that limit their performance as reagents. The detection systems of the present invention find use in many commercial products including homogeneous (competitive or sandwich) immunoassays, high throughput screening, protein arrays, PCR product detection and quantitation in real-time and hybridization detection, to name a few representative applications. As such, the subject invention represents a significant contribution to the art. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope.

Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a metal/conductive polymer composite colloid, said method comprising:
   combining:
   (i) a pre-formed metal colloid comprising a noble metal colloid; and
   (ii) a water-soluble conductive polymer;
   under conditions sufficient for said water-soluble conductive polymer to adsorb to metal particles of said pre-formed metal colloid to produce a metal/conductive polymer composite colloid.

2. The method according to claim 1, wherein said pre-formed metal colloid and said water-soluble conductive polymer are combined with agitation.

3. The method according to claim 2, wherein said pre-formed metal colloid and said water-soluble conductive polymer are combined by combining a first volume of said pre-formed metal colloid with a second aqueous volume of said water-soluble conductive polymer.

4. The method according to claim 3, wherein said pre-formed metal colloid and said water-soluble conductive polymer are combined by introducing said first volume into said second volume while said second volume is agitated.

5. The method according to claim 3, wherein said pre-formed metal colloid and said water-soluble conductive polymer are combined by introducing said second volume into said first volume while said first volume is agitated.

6. The method according to claim 1, wherein metal particles of said pre-formed metal colloid and said water-soluble conductive polymer are oppositely charged.

7. The method according to claim 6, wherein said metal particles are negatively charged.

8. The method according to claim 6, wherein said pre-formed metal colloid and said water-soluble conductive polymer are combined by combining a first volume of said pre-formed metal colloid with a second aqueous volume of said water-soluble conductive polymer.

9. The method according to claim 8, wherein said first and second volumes have a respective pH that is chosen so that said metal particles and water-soluble polymer are oppositely charged.

10. The method according to claim 3, wherein said second volume has a water-soluble conductive polymer concentration that provides for substantially no free water-soluble polymer in said metal/conductive polymer composite colloid.

11. The method according to claim 1, wherein said method further comprises modifying surfaces of particles of said metal/conductive polymer composite colloid to display a ligand.

12. The method according to claim 1, wherein said noble metal is chosen from gold and silver.

13. The method according to claim 12, wherein said noble metal is gold.

14. The method according to claim 1, wherein said water-soluble conductive polymer is an organic polymer.

15. The method according to claim 14, wherein said organic polymer comprises ionizable moieties.

16. The method according to claim 15, wherein said ionizable moieties are carboxylic acid moieties.

17. The method according to claim 1, wherein said water-soluble conductive polymer is a substituted polyaniline.

18. The method according to claim 17, wherein said substituted polyaniline is poly(aniline-2-carboxylic acid).

19. The method according to claim 1, wherein the density of said pre-formed metal colloid ranges from about 1.01 to about 1.30.

20. The method according to claim 1, wherein said pre-formed metal colloid comprises metal particles having a diameter ranging from about 1 nm to about 1 μm.

21. The method according to claim 1, wherein said pre-formed metal colloid is homogenous with respect to size of metal particles thereof.

22. The method according to claim 3, wherein the concentration of water-soluble conductive polymer in said second volume ranges from about 0.02 g/100 ml to about 2 g/100 ml.

23. The method according to claim 22, wherein said water-soluble conductive polymer of said second volume has an average molecular weight ranging from about 1,500 Da to about 32,000 Da.

24. The method according to claim 23, wherein said second volume is homogenous with respect to said water-soluble conductive polymer.

25. The method according to claim 11, wherein said ligand is a nucleic acid.

26. The method according to claim 11, wherein said ligand is a peptide.

27. The method according to claim 11, wherein said ligand is a small molecule.

28. The method according to claim 27, wherein said small molecule is an organic molecule.

29. The method according to claim 27, wherein said small molecule is an inorganic molecule.

30. A method of producing a metal/conductive polymer composite colloid, said method comprising:
combining:
(i) a first volume of a pre-formed metal colloid comprising noble metal particles suspended in an aqueous medium; and
(ii) a second volume of a solution of a water-soluble conductive polymer;
under conditions sufficient for said water-soluble conductive polymer to adsorb to metal particles of said pre-formed metal colloid to produce a metal/conductive polymer composite colloid;
wherein said second volume has a water-soluble conductive polymer concentration that provides for substantially no free water-soluble polymer in said metal/conductive polymer composite colloid.

31. The method according to claim 1, further comprising: preparing the pre-formed metal colloid.

* * * * *

UNITED STATES PATENT AND TRADEMARK OFFICE
CERTIFICATE OF CORRECTION

PATENT NO. : 7,618,560 B2 Page 1 of 1
APPLICATION NO. : 11/264353
DATED : November 17, 2009
INVENTOR(S) : Englebienne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 700 days.

Signed and Sealed this

Twenty-sixth Day of October, 2010

David J. Kappos
*Director of the United States Patent and Trademark Office*